United States Patent [19]

Raven et al.

[11] Patent Number: 4,917,486
[45] Date of Patent: Apr. 17, 1990

[54] PHOTOCOAGULATION APPARATUS

[75] Inventors: Anthony Raven, Royston; John Marshall, Farnborough, both of England

[73] Assignee: Scientific Generics Ltd., Cambridge, England

[21] Appl. No.: 196,320

[22] Filed: May 20, 1988

[30] Foreign Application Priority Data

May 20, 1987 [GB] United Kingdom ............ 8711888
Aug. 12, 1987 [GB] United Kingdom ............ 8719131
Mar. 16, 1988 [GB] United Kingdom ............ 8806254

[51] Int. Cl.⁴ .................................. A61B 3/10
[52] U.S. Cl. ........................... 351/221; 606/40; 606/4
[58] Field of Search ............ 351/221, 208, 214; 128/303.1, 395

[56] References Cited

U.S. PATENT DOCUMENTS 3,096,767  7/1963  Gresser et al. .
3,512,868  5/1970  Gorkiewicz .
3,551,029 12/1970  Kirchhoff .
3,703,176 11/1972  Vassiliadis et al. .
4,580,559  4/1986  L'Esperance ............ 128/303.1

FOREIGN PATENT DOCUMENTS 0221649  5/1987  European Pat. Off. .
2202120  1/1972  Fed. Rep. of Germany .
3041969  5/1981  Fed. Rep. of Germany .
3341455 11/1983  Fed. Rep. of Germany .
0131768  1/1985  Fed. Rep. of Germany .
8401110  3/1984  PCT Int'l Appl. .
2065919 11/1981  United Kingdom .

OTHER PUBLICATIONS

R. Brancato SPIE vol. ECOOSA '86/365.
C. A. Puliafito Arch Ophthalmal-vol. 105, Mar. '87, "Laser & Applications" Aug. '87/38.

Primary Examiner—P. M. Dzierzynski
Attorney, Agent, or Firm—Chilton, Alix & Van Kirk

[57] ABSTRACT

The invention provides a photocoagulator using an infrared laser diode source (70). A dichroic beam splitter (68) is used to combine the optical path of the laser system with the viewing system. Such an arrangement affords the clinician an uninterupted, uncolor view of the patient's eye during treatment, without any risk of damage to the clinician's eye. There is also provided an alignment system using a visible laser diode (80). The alignment system may include a number of mutually non parallel beams which pass through different portions of the pupil and provide information on aim, focus and vignetting.

26 Claims, 7 Drawing Sheets

PHOTOCOAGULATION APPARATUS

This invention relates to photocoagulation apparatus using lasers. Such photocoagulation apparatus may also be used for therapies which do not actually involve coagulation but may be performed with the same apparatus.

Laser photocoagulation has become a standard ophthalmic procedure for the treatment of a number of retinal disorders. Because of the size, complexity and cost of current laser photocoagulators, their use is restricted to fixed installations in the larger centres which can offer the technical and financial resources needed to support their operation.

Photocoagulation is used for a range of eye disorders including retinal vascular problems (e.g. diabetic retinopathy), choroidal vascular problems and macular lesions (e.g. senile macular degeneration). In the first of these the requirement is to place many hundred of lesions into the peripheral retina with sizes of up to 500 microns to destroy the outer retinal layers. On the other hand, for macular lesions, a few precisely placed small lesions are required to seal leakage from the pigment epithelium and to destroy sub-retinal vessels. Irradiation times per lesion are typically 0.2-1 secs and irradiation powers of 0.1-2 watts.

By far the majority of laser photocoagulation is currently carried out using conventional Ar or Kr ion lasers. These lasers, emitting in the blue/green and yellow/red regions of the spectrum respectively, are sources of more than sufficient levels of power for photocoagulation but are inefficient (e.g. around 0.01%) requiring up to 40 kW of three phase power and associated water cooling to remove the heat load. In addition the systems are bulky, both in terms of the laser head and power supply, and technically complex (high voltage, vacumm tubes etc). These combine to require a fixed installation system with a high level of services and technical support.

A problem with such photocoagulators is that the retina cannot be directly viewed by the clinician during irradiation since potentially damaging scattered and reflected laser light would enter the eye of the clinician. In practice therefore, conventional systems all have a mechanical shutter interposed on the viewing channel during irradiation which is undesirably mechanically complex, is of finite mechanical reliability and does not allow a continuous view of the retina. This has proved hazardous to the clinician's vision, due to shutter failure.

According to one aspect of the present invention, there is provided a laser photocoagulator including a laser system and a viewing system, characterised in that the laser system includes a laser source which operates in the infrared range, and said viewing system and said laser system have in common a dichroic beam splitter which, in use, seperates infrared light from visible light, said viewing system and said laser system sharing a substantially common ray path between said dichroic beam splitter and the eye of a patient, whereby the clinician may view a patient's eye through the beam splitter substantially without risk of exposure to the infrared laser light used for treatment.

The invention provides a system which allows the retina of the patient to be continuously observed by the clinician during the treatment without any risk of the laser light reflected from the retina of the patient damaging the eye of the clinician. By virtue of the substantial coincidence between the optical axes of the viewing system and the laser system between the patient's eye and the dichroic beam splitter, the clinician using the photocoagulator is able to aim the laser spot with great precision and without loss of view at the time of firing the laser. This is particularly important for treatment of the macular region. In addition, since substantially all the visible wavelength light reflected from the retina is allowed to reach the eye of the clinician, the view of the retina has its normal colours.

The most significant difference in terms of the photobiology of the present system from standard systems is the use of the longer wavelength light from an infrared laser source. The use of the Ar ion laser from 1968 made use of the strong absorption of the green laser light by the haemoglobin in the retinal capillaries. This then led on to the development of a tunable dye laser system to match more closely the wavelength of the light to the haemoglobin absorption. However subsequent research has shown that, because of the small size of the capillaries (around 10-12 microns), the energy absorbed by the capillaries is insufficient to cause a significant effect and the main photobiological effect arises from damage to the pigment epithelium.

While theoretically it should be possible to adjust the specific site of absorption by selection of the wavelegth, in practice it is impossible to distinguish between super-threshold burns at different wavelengths within the range from Argon to laser diode wavelengths because of the spread in damage due to thermal conduction. The longer wavelengths do however show greater penetration depth, and this becomes significant at about 1064 nm (Nd:YAG), but at 800-830 nm the absorption depth in the retinal pigment epithelium is sufficiently small to produce substantially the same effects as the currently used sources (see FIG. 1). By using an infrared laser source producing light at what might be at first considered an unfavourably long wavelength the laser light can be effectively filtered in relation to protecting the practitioner's eye without changing the visible spectrum of reflected light. This allows the retina to be clearly viewed before and during irradiation, while the laser light is sufficiently close to the wavelength of a Krypton or dye laser to virtually indistinguishable in biological effect. Advantageously therefore, the wavelength of the infrared laser light is close enough to the visible spectrum to be indistinguishable in biological effect whilst being far enough outside the visible spectrum to allow efficient filtering.

Preferably the light is at a wavelength of substantially 800 nm which is a significantly longer wavelength than Ar or Kr lasers.

Preferably the laser light source comprises an infrared solid state laser diode. These laser diodes offer a small, reliable and relatively low cost source of laser light that may be used for retinal photocoagulation. The size and power consumption of these diode lasers are such that a hand held and/or portable photocoagulation unit consuming a few watts of electrical power may be produced. Recent developments aimed at the printing industry have raised the power levels of laser diodes to 2-500 mW continuous output which is sufficient to achieve photocoagulation. Typical operating power levels of a laser in a conventional system for retinal applications are several hundred milliwatts. This power level has recently become available in semiconductor laser diodes developed by Spectra Diode Labs in the USA (a joint venture of Spectra Physics and Xerox) and Sony in Japan.

Advantages of the laser diode for these applications are the cost (around 10–20% of that of an Ar laser), the efficiency (around 30%, providing sufficient optical output using only a few watts of low cost, low voltage electrical power e.g. from a battery), the lack of a need for water cooling, and the size, (the laser fits into a transistor type package). These factors combine to make feasible a small hand held and/or portable photocoagulator which can be run, if necessary, from a portable battery power unit and requiring a minimum of service and technical support. Such photocoagulators provide major operational advantages over current ion laser units.

The function of the dichroic beam splitter is to separate the infrared laser light from the visible light with minimal chromaticity changes in the visible light from which the image of the retina available to the clinician is formed. The term "dichroic beam splitter" encompasses long pass mirrors (i.e. those which transmit only wavelengths above a given value), short pass mirrors (which transmit only wavelengths below a given value), and band pass mirrors which transmit only a band of wavelengths. It is important that the dichroic beam splitter should preferably either reflect (or transmit) with high efficiency at the infrared laser diode wavelength and transmit (or reflect, respectively) the visible spectrum.

It is a preferred feature of the present invention that the dichroic beam splitter should be of the type which reflects infrared light and transmits visible light. This feature allows the laser system of the photocoagulator to be simply and effectively coupled to the viewing system of what might otherwise be a standard ophthalmoscope or slit lamp viewing system.

The light produced by a laser diode is emitted from the region of the diode junction, which at the end face of the laser may be typically 100 micrometers by 1 micrometer in size. This laser light may then be collimated and subsequently focused onto the retina of the patient. The size of the image of laser diode emitting region produced on the retina must not be too large since as the size of the image increases, the intensity of the light decreases and the exposure time or laser power necessary to produce the desired effect rises unfavourably. This problem is most important in relation to the size of the image in the 100 micrometers direction. Accordingly it is a preferred feature of the invention that the laser system of the photocoagulator includes means for reducing the magnification in one direction of the image of the infrared laser source which, in use, is produced on the retina. The image magnification reducing means may for example comprise an anamorphic prism pair arranged so as to reduce the magnification of the image in its longest direction.

Another problem which may lead to an increase in the necessary exposure time or laser power is vignetting of the infrared laser beam by the iris of the eye. If the diameter of the infrared laser beam as it passed through the eye is reduced, this helps the problem of vignetting but has the effect of increasing the size of image on the retina, which as explained above is undesirable. Thus, a preferred feature of the invention is that the laser system of the photocoagualtor includes optical means providing an optimum beam diameter of the infrared laser light which, in use, passes through the pupil of the patient's eye, so that the light intensity of the image of the infrared source may be maximised. The means may, for example, comprise a telescope.

Another preferred feature helpful in avoiding the problem of vignetting is the provision of an aligning system which may be used to ensure that the infrared laser beam will not be vignetted by the iris when the infrared laser diode is fired. It is particularly advantageous to use an alignment system incorporating a visible laser diode. By "visible laser diode" is meant any form of laser diode which provides ready visible laser light. The alignment system may give the clinician an indication of any vignetting by the iris or the point at which the photocoagulator is aimed or both. Such visible laser diodes provide a particularly compact and high intensity light source capable of being simply and effectively combined with the rest of the photocoagulator system. According to a preferred feature, the invention provides a laser photoagulator wherein the laser system further includes an alignment system incorporating a visible laser diode.

A particularly advantageous way in which the alignment system may be combined with the rest of the laser system of the photocoagulator is to use a dichroic beam combiner or polarising beam combiner so arranged as to cause the visible laser light from said alignment system to share the same optical path with the infrared laser light between said dichroic beam combiner or polarising beam combiner and the eye of the patient. This arrangement is both simple and inexpensive to construct whilst being accurate and reliable.

In a simple form, the alignment system may be constructed so as to focus a single beam of visible light onto the retina at the point where the infrared light will be incident when the photocoagulator is fired.

Another problem associated with photocoagulation systems is that of ensuring that the infrared laser light is accurately focused on the patient's retina. A desired feature of the alignment system of the present invention is that it is capable of providing information to the clinician concerning both the alignment of the system with the iris of the patient and whether or not the laser system is focused on the retina.

Accordingly, a preferred feature of the alignment system is that, in use, a plurality of beams of visible light are incident on the retina, said beams being arranged to pass through different portions of the pupil such that if said photocoagulator is misaligned with the pupil at least one of the beams will be at least partly blocked by the iris, and the pattern of the beams on the retina being indicative of whether or not the laser system is focused on the retina.

According to one embodiment, the alignment system provides a plurality of beams which converge to a spot on the retina when the laser system is focused on the retina.

According to another embodiment, the alignment system provides a plurality of beams which are mutually non-parallel, the relative positions of said beams when incident on the retina being dependent upon whether or not the laser system is focused on the retina. Another preferred feature is that each of said beams has a non-ciruclar cross-section when incident on the retina, the relative alignment of the shapes produced on the retina being dependent on whether or not the laser system is focused on the retina. For example, the beams may produce two or more rectangles on the retina with the alignment of the axes of the rectangles being dependent on whether or not the laser system is focused on the retina. Preferably the shaped beams are provided by illuminating a target with a plurality of nonparallel collimated beams of light. The nonparallel collimated beams may be conveniently provided by one or more split field screens.

A particularly preferred embodiment has four mutually nonparallel beams which produce a cross shaped pattern when the laser system is focused on the retina. The target required to produce such a pattern of beams may be a circular disc formed with four slits disposed on orthogonal radii and extending inwards towards, but without reaching, the centre of said disc. This embodiment may also include a pair of split field screens disposed on the optical axis of alignment system, the second of the screens being rotated by 90° with respect to the first. These screens are preferably close to and may be incorporated in the target disc.

The photocoagulator of the present invention may have a viewing system similar to either a standard direct or indirect ophthalmoscope or slit lamp.

In a preferred embodiment, the photocoagulator may be provided as an add-on component to such standard viewing systems. This feature minimises the cost of producing the photocoagulator and allows it to be used with illumination and viewing systems with which the clinician is already familiar.

The use of infrared laser diode sources makes possible a portable direct or indirect ophthalmoscope modified for use as a photocoagulator. The system may be based on a direct opthalmoscope to view the retina with the laser diode and associated optics built into the handle of the ophthalmoscope and powered from batteries or a small power supply unit. Aiming onto the retina would be using either a projected light spot or target from a separate system, or preferably the alignment system described above. The laser diode light is coupled into the system using a dichroic beam splitter in front of the eye piece. If the power from one diode is not sufficient for photocoagulation, then two laser diodes can have their outputs combined using, for example, a polarising beam combiner. This laser system preferably further includes a half-wave plate in between one of the laser diodes and the polarising beam combiner to ensure the far field radiation patterns of the lasers overlie one another.

It is apparent that the alignment system described above may be used in any form of photocoagulator. The operational advantages of a system which simultaneously provides information on the alignment with the iris and the distance from the retina are considerable. A number of different visible light sources may be used for the alignment system such as tungsten or halogen bulbs, but it is strongly preferred to use a visible laser diode which gives the advantages discussed above.

Viewed from another aspect the invention provides an alignment system for a photocoagulator, the system producing, in use, a plurality of beams of visible light which are incident on the retina, said beams being arranged to pass through different portions of the pupil, such that if the photocoagulator is misaligned with the pupil at least one of said beams will be at least partly blocked by the iris, and the pattern produced by said beams on the retina also being indicative of whether or not the photocoagulator is focused on the retina.

A preferred feature of this aspect of the invention is that the light source for the alignment system comprises a visible laser diode.

Viewed from a further aspect the invention provides a laser photocoagulator including an alignment system incorporating a laser diode providing an output in the visible range of wavelengths, preferably 400 to 700 mm.

Embodiments of the invention will now be described, by way of example only, with reference to the accompanying drawings wherein.

Figure 7:
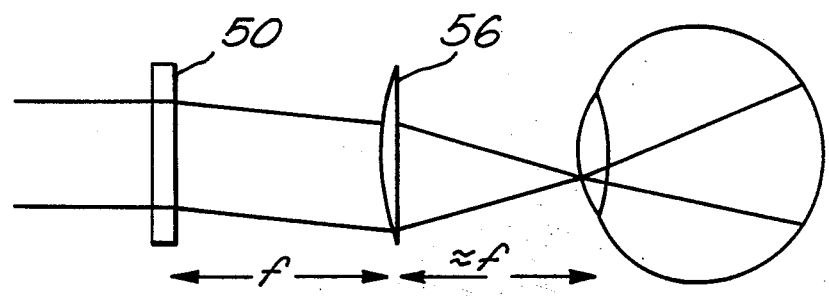
FIG. 7 illustrates schematically a preferred optical aiming system of this invention.
Figure 8:
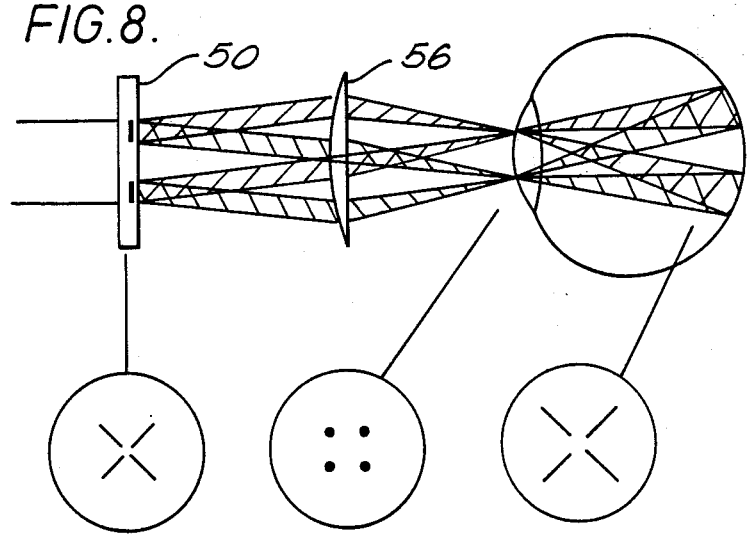
Figure 8:
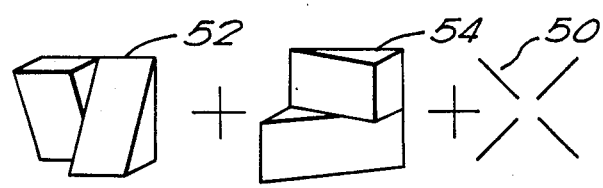
Figure 9:
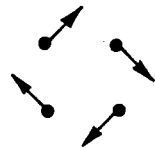
Figure 10:
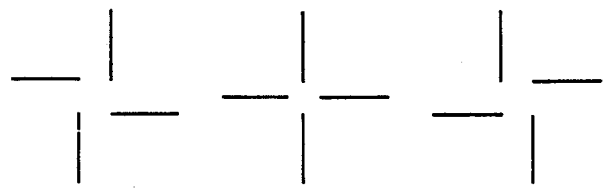

FIG. 8 corresponds to FIG. 7 but shows, in addition, the nature of the target and images of the target at the patient's cornea and retina;

FIG. 9 shows part of the optical system used in the system of FIGS. 7 and 8;

FIG. 10 illustrates how the image of the target appears to a clinician during focussing of the laser photocoagulator.

Figure 11:
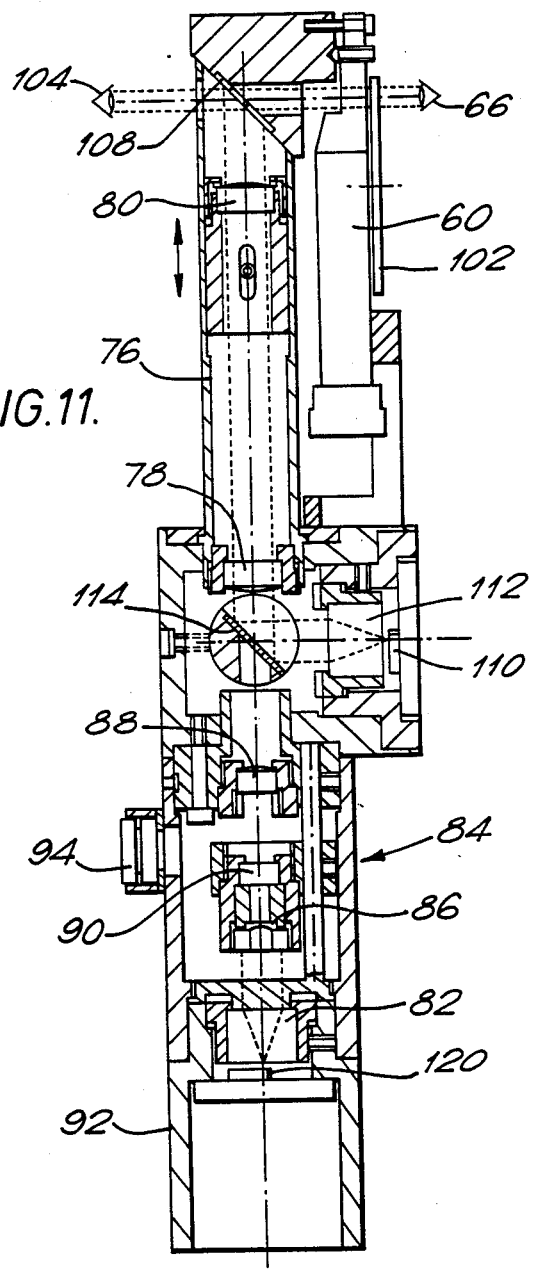

FIG. 11 is a cross-sectional view of a photocoagulator adapted to use the illumination and viewing systems similar to an ophthalmoscope.

Figure 12:
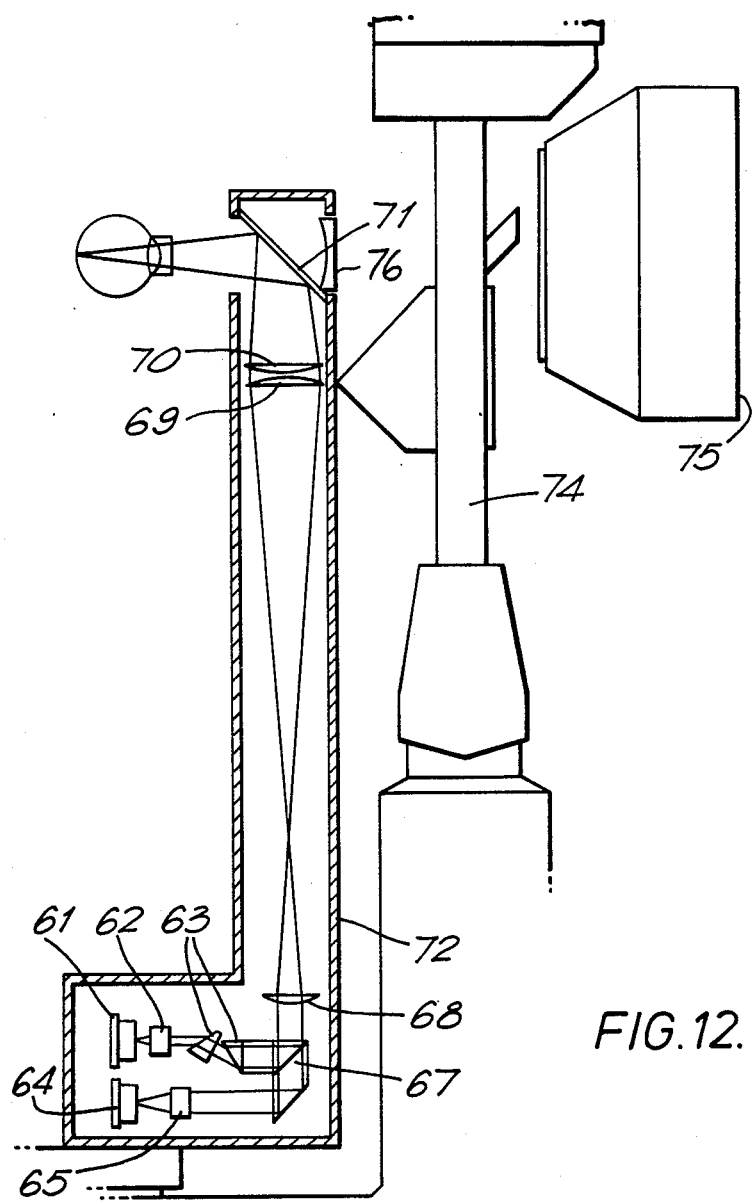

FIG. 12 shows a cross-sectional view of a photocoagulator adapted to use the illumination and viewing system of a slit lamp.

Figure 1:
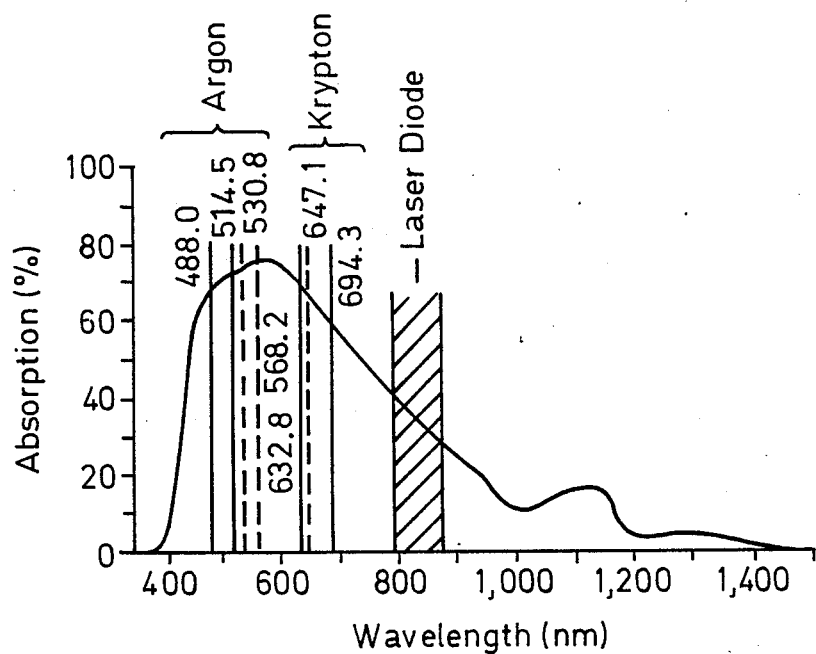
FIG. 1 illustrates the absorption of human retinal pigment epithelium at various wavelengths.

Referring to FIG. 1, the percentage absorption of human retinal pigment epithelium is shown for various wavelengths. The positions of the wavelengths of argon, krypton, helium-neon, ruby lasers and infrared diode lasers are shown. The absorption curve is extended beyond 1400 nm demonstrating the decrease in absorption with increasing wavelength.

Figure 2:
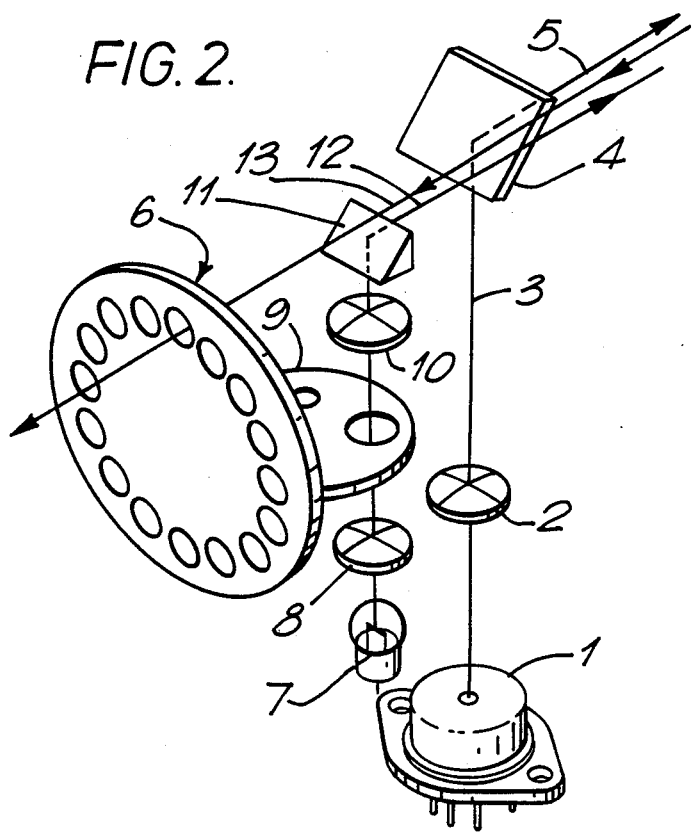
FIG. 2 is a diagrammatic illustration of the optics of a portable hand-held photocoagulator in accordance with the present invention.

Referring now to FIG. 2, the optical components in one embodiment of a portable hand-held photocoagulator in accordance with the invention comprise an infrared laser diode 1 whose output passes through collimating and focusing optics 2 (represented schematically by a single lens). Beam 3 then passes to a dichroic beam splitter 4 which reflects beam 3 towards the patient. The viewing system may include a conventional focusing arrangement 6. The illuminating system included in the photocoagulator comprises a tungsten bulb 7, a condenser lens or lens system 8, an aperture/filter disk 9, a projection lens 10, and a prism 11. In use, light from the tungsten bulb 7 passes through optical components 8, 9 and 10 to reach prism 11 from which it emerges along axis 12. The light from the tungsten bulb emerges from the apparatus and enters the eye of a patient. Diffuse reflection by the retina of the patient results in light being returned to dichroic beam splitter 4 along axis 13, which transmits the visible light to an eye piece (not shown) where the clinician is able to view directly the patient's retina. The dichroic beam splitter, alone or in conjunction with other optical filter components, serves to protect the practitioner's eye from the laser radiation. The aperture and filter piece 9 may include suitable target markings for aiming the laser beam 3. When the apparatus is properly aligned, the practioner actuates infrared laser diode 1 which emits a regulated pulse of laser radiation at a wavelength of approximately 800 nm. This passes along the optical system to the dichroic beam splitter 4 where it is reflected along axis 5 and travels into the eye of the patient. With this optical system, the clinician is able to observe the patient's retina during laser treatment, without being subjected to potentially harmful reflected laser light. Because of the small size of the solid state infrared laser diode 1, the entire optical system can be housed conveniently in a casing resembling a typical hand-held direct ophthalmoscope.

Figure 3:
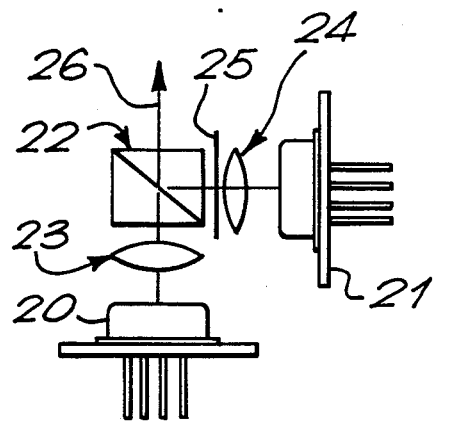
FIG. 3 shows a modification of the apparatus of FIG. 2 to facilitate operation at higher power levels.

Referring to FIG. 3, in a modified arrangement two laser diodes 20 and 21 are located with their output axes disposed orthogonally and so as to be coincident on a polarising beam combiner 22. Conventional collimating optics 23 and 24 are interposed between the laser diodes and beam combiner 22. An optional half-wave plate 25 is also positioned between collimating system 24 and beam combiner 22. By means of this arrangement, a laser output beam 26 may be obtained of a power level greater than that possible with a single laser diode. The half wave plate allows the two beams to be combined using polarization while overlaying far field irradiation patterns in the same sense. This may be advantageous where the far field pattern of the laser diode is not axially symmetric.

Figure 4:
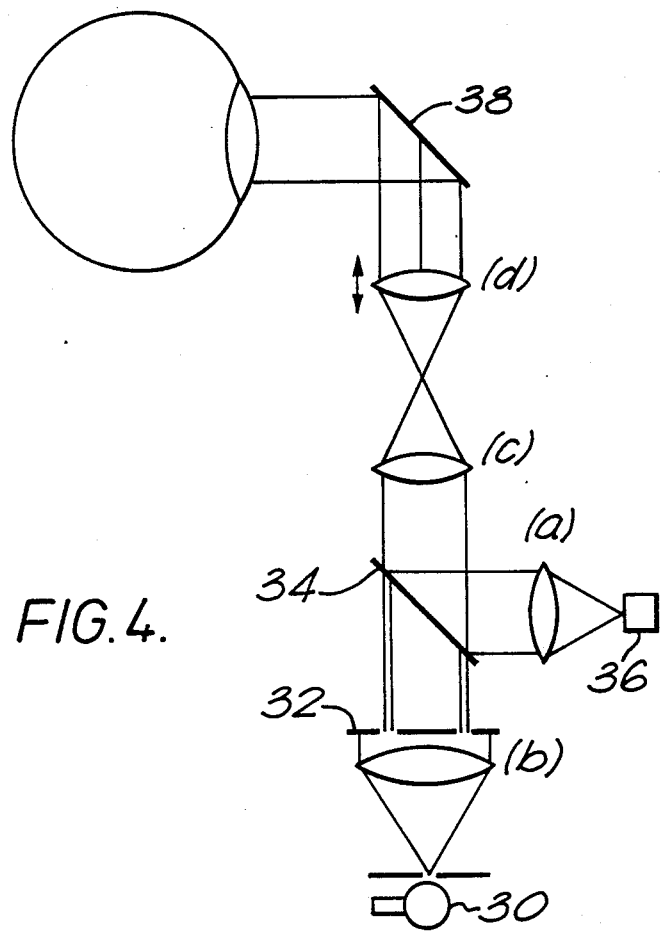
FIG. 4 shows a further embodiment of the optical system for a portable hand-held photocoagulator in accordance with the present invention.

Referring next to FIG. 4, an alignment optical system, in accordance with a preferred embodiment of this invention, is shown. Here, the light from a high intensity light source 30 is directed to a collimator lens (b) and thence to a mask 32 defines a pair of parallel beams of visible light. The light source 30 illustrated comprises a tungsten bulb, although again, in a modified arrangement, the source is preferably in the form of a laser diode producing light in the visible spectrum. After passing through the mask 32, it reaches a first dichroic beam splitter 34 which transmits the visible light. An infrared laser diode 36 is provided as shown and its output is directed via lens (a) onto the first dichroic beam splitter, where it is reflected and thus follows the same optical path as does visible light from the light source 30. A second dichroic beam splitter 38 is located further along the optical path and is separated from the first dichroic beam splitter by two lenses (c) and (d). Lens (a) and the mask 32 are equidistant from lens (c).

During treatment the patient's eye is focused at infinity. If the patient's eye has zero refractive error then the parallel beams of light entering the eye will be focused to a point on the retina. However, if the patient is either long or short sighted then the parallel beams of light will not be focused to a point on the retina. In this embodiment the clinician is able correct for this by adjusting the beams of light reflected off the second dichroic mirror 38 to be either slightly convergent or divergent depending on the nature of the patient's refractive error. This adjustment is achieved by moving lens (d) forward or backward along the optical axis. Lenses (c) and (d) form a telescope and by changing the distance between the lenses the collimated beam of light incident on lens (c) will emerge from lens (d) as either a divergent, collimated or convergent beam. Since the collimated light from both the infrared laser diode 36 and the mask 32 is combined by first dichoric beam splitter 34 then the telescope formed by lenses (c) and (d) will have the same effect on both the visible and infrared light and the images of the visible and infrared light will be confocal at the eye.

Figure 5:
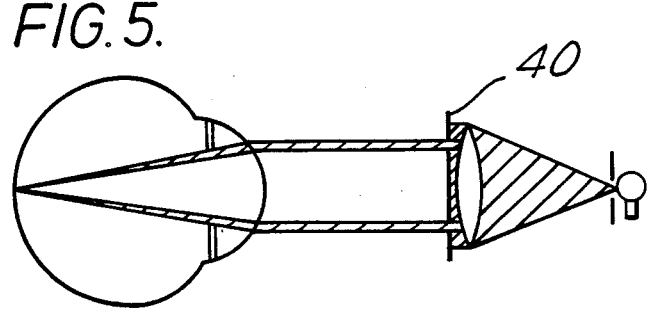
FIG. 5 illustrates the focusing arrangement incorporated in the optical system of FIG. 4.
Figure 6:
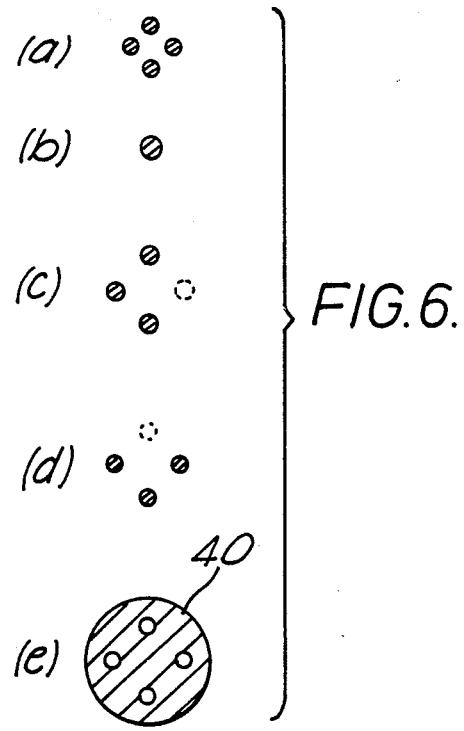
FIG. 6 illustrates how the system of FIG. 5 may be used.

FIGS. 5 and 6 illustrate how the focusing system may be used with a mask 40 having four apertures arranged equidistant from the centre of the mask and on orthogonal diameters thereof (as shown in FIG. 6(e)). The mask 32 produces four collimated beams of light. These beams are combined with the infrared light by first dichoric beam splitter 34 and are arranged to follow a path through the rest of the system corresponding to the outer peripheral region of the infrared beam (as can be seen in FIG. 4). This system can then be used to indicate to the clinician whether or not lens (d) is correctly adjusted to correct for any refractive error in the patient's eye and whether or not the photocoagulator is correctly aligned with the patient's eye so that none of light is vignetted by the iris. When these conditions are met, the clinician will observe a single, central spot as shown at FIG. 6(b). When the image is out of focus, the four apertures of the mask are separately visible as four spots, as at FIG. 6(a). Misalignment causes one or other of the spots to "disappear" as illustrated at (c) or (d) for horizontal and vertical misalignment respectively. In practice the clinician will adjust the alignment of the photocoagulator with the eye until all four spots are visible and will then adjust the position of lens (d) until the four spots overlap to form a single spot indicating that the photocoagulator is focused on the retina. Thus it will be seen that this arrangement enables accurate focusing and aiming of the infrared laser beam and also correct alignment with respect to the pupil. It will be appreciated that, with this arrangement when the system is correctly focused, the spots all overlap and it is no longer possible to see if the photocoagulator is correctly aligned. This problem is overcome by the modified alignment system described below.

Referring to FIG. 7, there is shown a further form of aiming, focusing and alignment system in one embodiment of the present invention. The system as a whole also provides three functions for the main (infra red) treatment laser, namely: (i) aiming; (ii) focusing; and (iii) alignment with respect to the iris, i.e. provides an indication of vignetting. The system comprises a target 50 which is illuminated by collimated light. The target 50 has four slits disposed on orthogonal radii as shown and is close to a pair of split field screens 52, 54 (see FIGS. 8 and 9) which are themselves disposed on the optical axis of the system but are rotated through 90° with respect to one another. The split field screens 52, 54 are positioned on the side of the target between it and the illumination source (not shown), which again is preferably a laser diode operating in the visible range of wavelengths, and the target 50.

Referring to FIG. 7, the imaging lens 56 is separated from the target 50 by a distance equal to the focal length of imaging lens 56. Thus, the imaging lens 56 produces an image of the target 50 at infinity. During treatment the patient's eye is focused at infinity and thus if the patient has zero refractive error a focused image of the target 50 will be produced on the retina. If, the patient has a refractive error then the image on the retina will be out of focus. As described above, in practice a telescope (not shown) will be provided between the imaging lens 56 and the patients eye. The clinician will then use this telescope to introduce the necessary amount of convergence or divergence in order that image of the target on the retina is in focus.

It is important that the clinician should be able to accurately and easily determine whether or not the image of the target 50 on the retina is in focus. This object is achieved by the illustrated system as a result of the manner of illumination of the target. As illustrated in FIG. 8, the combination of the target 50 and the split field screens 52, 54 produces four nondivergent but mutually nonparallel beams of light emerging from the target. The effect of this is that when the image of the target on the retina is out of focus, not only does the outline of each slit become blurred but the image of that slit is displaced to one side as illustrated in FIG. 10. Thus the clinician does not have to rely on judging whether or not the image of each slit is sharply defined (which is difficult) but can instead adjust the telescope so that the overall image of the target on the retina is undistorted.

Another object of the system is to provide the clinician with an indication of whether or not the infrared laser light will be vignetted by the iris. As shown in FIG. 8, each of the four beams is arranged to pass through a different portion of the retina. As described in relation to the embodiment of FIGS. 4, 5 and 6, the four beams will be arranged to coincide with the peripheral region of the infrared beam as it passes through the pupil. The photocoagulator will typically be held at a distance from the eye which makes the distance between the imaging lens 56 and the eye approximately equal to the focal length for the imaging lens 56. Thus, the four beams will be typically focused to four spots at the pupil. If the photocoagulator is misaligned then one or more of the spots will be vignetted and consequentley one or more of the slits will be missing from the image on the retina. The system shown in the Figures uses a single imaging lens 56 but it will be apparent to those skilled in the art that a lens system comprising more than one lens producing a system with different front and back focal lengths could be used.

In the summary, the system shown in FIGS. 7 to 10 gives rise to the following effects:

1. The image at the cornea consists of four spots, as shown in FIG. 8. Provided that the four collimated beams which strike the target all make the same angle with the optical axis, as will be the case when the illuminating source and the target are disposed orthogonally, and the imaging lens is properly positioned, then the four spots at the cornea will be equally spaced from the centre of the cornea.

2. Since each section or slit of the target corresponds to a given one of the four spots at the cornea, if the light ray corresponding to any one of these spots is interrupted by the patient's iris, i.e. if there is vignetting, then this will be observed by the clinician who will see that part of the image of the target is absent from the image which he sees on the patient's retina.

3. The centre of the target (as seen by the clinician on the patient's retina) provides a pointing or aiming facility for the infrared treatment laser.

4. Since the principal rays for each segment of the target have different orientations with respect to the optical axis, a change in focus will cause a change in the shape of the observed pattern on the retina.

In the present embodiment, the four collimated beams are generated by the pair of split field screens 52, 54 shown in FIG. 9. This Figure also shows the resultant beam directions of the light emerging from the target 50.

FIG. 10 shows how the resultant image at the retina varies as it is moved through focus. The middle of the three images corresponds to correct focusing.

With a target 200 micrometers in width, it is possible to adjust the focus at the retina such that alignment is 0±40 micrometers. The alignment system illustrated produces four spots of approximately 0.5 mm diameter on a 3.5 mm diameter circle. The principal rays therefore converge at an angle of 3.5/25=0.14 radians (the back focal distance of the eye is 25 mm). The focus is therefore adjusted to ±300 micrometers. For an infrared treatment laser, the required depth of field is 0.5 mm; the system described above is therefore more than adequate for use with such a source.

As mentioned earlier, the source of illumination for the aiming system is preferably a visible laser diode.

The manner in which this alignment system can be combined with the other components of a photocoagulator will now be discussed.

FIG. 11 shows a photocoagulator adapted to use the illumination and viewing systems of an ophthalmoscope.

The photocoagulator viewing system uses a standard ophthalmoscope head 60, which includes a lens wheel for compensation of the combined refractive error of the patient's and clinician's eyes 104, 66. A first dichroic mirror 68, which reflects infrared light and transmits visible light, is disposed in the viewing system between the patient's and clinician's eyes 104, 66. The ophthalmoscope head 60 also includes the illumination system (which may be as shown in FIG. 2).

The photocoagulator laser system includes an infrared laser diode 110, a first high numerical aperture collimating lens 112, a second dichroic mirror 114, and a telescope 76. The telescope comprises a fixed lens 78 and a slidably mounted lens 80. The second dichroic mirror 44 is constructed to reflect infrared light and transmit visible light.

The photocoagulator alignment system includes a visible laser diode 120, a second high numerical aperture collimating lens 82 and an alignment optics assembly 84. The alignment optics assembly 84 includes two lenses 86, 88 and a target and split screen assembly 90 as illustrated in FIGS. 7 to 10.

The power source for the photocoagulator may comprise batteries (not shown) stored in the handle 92 or a separate control unit. A firing trigger 94 is positioned on the front of the photocoagulator and is used to control the operation of the infrared laser diode 110.

The function of the illumination and viewing systems is to provide the clinician with a continuous uncoloured view of the patient's retina during treatment. The first dichoric mirror 108 allows visible light reflected from the retina of the patient's eye 104 to reach the clinician whilst blocking the passage of any harmful infrared light.

The laser system provides a high intensity beam of infrared light which the clinician can use to produce the required effect on the retina of the patient's eye 104. The first high numerical aperture lens 112 serves to collect and collimate the infrared light produced by the infrared laser diode 110 when this is fired by trigger 94. The second dichoric mirror 114 reflects the infrared light through the telescope 80 to the first dichroic mirror 108, whilst transmitting the visible light from the alignment system so that this then passes along the same optical path as the infrared light. The function of the telescope 80 is to allow the infrared laser light to be focused onto the retina of the patient's eye 104.

The alignment system operates as described above to provide four nondivergent mutually nonparallel beams of light. The visible light from the alignment system is combined with the infrared light by second dichroic mirror 44. The telescope 80 acts in the same way on both the visible and infrared light and is used by the clinician as described above to ensure the photocoagulator is correctly aimed, focused and aligned with respect to the eye.

In use the clinician observes the retina of the patient's eye 104 through the lens wheel 102, and first dichroic mirror 108. The clinician then rotates the lens wheel 102 until the desired refractive correction is achieved and a focused image of the patient's retina is seen.

The visible laser diode 120 of the alignment system produces visible light which is collected and collimated by second high numerical aperture lens 82 and then passes to the alignment optics assembly 84. The alignment optics assembly 84 produces four mutually nonparallel beams of visible light as a result of the action of the lens 86, 88 and the target and the split screen assembly 90. These four beams are then transmitted through the second dichroic mirror 108. Although first dichoric mirror 68 is of a type which transmits rather than reflects visible light, the visible laser diode 120 is sufficiently bright that the small amount of visible light which the first dichoric mirror 108 reflects is enough to produce an image on the retina of the patient's eye 104 which is visible to the clinician.

The clinician then moves slidable lens 80 to adjust the focus of the visible light on the retina by observing the pattern of the image on the retina as is shown in FIG. 10. Since the visible light and the infrared light share the same path from the second dichroic mirror 114 to the patient's eye 104 then if the visible light is focused, the infrared light, when produced, will also be focused. The clinician simultaneously checks for vignetting by ensuring that the whole of the pattern is visible and also aims the photocoagulator at the desired part of the retina.

When satisfied with the focusing, alignment and aim of the system the clinician pulls the trigger 94 and the infrared laser diode 110 produces a regulated pulse of high intensity light which is collected and collimated by the first high numerical aperture lens 112. The collimated infrared light is then reflected from the second dichroic mirror 114, passes through the telescope 76 and reflects from the first dichroic mirror 108 into the patient's eye 104. The clinician can then move on to treat another part of the retina by repeating the aiming, aligning and focusing procedure.

FIG. 12 illustrates an alternative form of photocoagulator which is adapted for use as an add-on demountable attachment for a slit lamp. Light from a high power infrared laser diode 61 is collimated by a high numerical aperture lens 62 to produce a collimated output beam. An anamorpohic prism pair 63 expands the beam along the long axis of the infrared laser diode output region and so reduces the image size on that axis at the retina by a corresponding factor. Where higher powers or intensities are required than can be achieved with a single laser diode, the beam from a second infrared laser diode can be combined with that of infrared laser diode 61 using a polarising cube as illustrated in FIG. 3. Light from a visible laser diode 64 is collimated by a lens 65, to produce a collimated beam, and combined with the infrared beam by dichroic cube 67. The combined visible and infrared beams are then relayed and expanded by telescope lenses 68 and 69 and focused to a point confocal with the slit lamp microscope 75 by lens 70. Lenses 62 and 65 can be adjusted to ensure confocality of the infrared and visible beams at the retina. To optimise the minimum achievable spot size at the retina and maximise the efficiency of energy delivery to the retina the anamorphic ratio of prisms 63 and the expansion ratio of telescope 68 and 69 must be carefully selected such that the beam is narrow enough to pass with minimal obstruction through the iris of the patient's eye, and the size of the image of the output region of the infrared laser diode 61 on the patient's retina is not too large. In addition, the efficiency is improved if the aperture of lens 62 is imaged by lenses 68, 69 and 70 onto the pupil. Wavelength selective mirror 71 is used to combine the optical path of the viewing system and the laser system and is designed to have a high reflectivity and low transmission for the infrared laser wavelengths and a high and essentially neutral transmission in the visible spectrum. Examples of such a mirror are mirrors known as hot mirrors, although other types of mirror such as a narrow band, high reflector mirror can also be used. Suitable mirrors can be made either by multilayer dielctric coatings or holographically in materials such as dichromate gelatin. Mirror 71 allows the operator to have a clear view of the retina throughout the procedure while being protected from laser radiation reflected from the patient's eye. The optical system is contained in a housing 72 which is mounted onto the tonometer mount 74 of the slit lamp and is demountable. A diverging lens 76 may be placed between the slit lamp and the patient's eye to move the focal point of the slit lamp further from the slit lamp. This has the advantage of allowing easier access by the clinician to the patient's eye.

When using this particular system, the clinician places a diverging lens on the patient's eye to compensate for any convergence produced by the cornea and lens of the eye. Then whilst continuously viewing the retina through the slit lamp microscope 75, the clinician can aim, align and focus the laser system to the desired point on the retina and then fire the infrared laser diode 61.

We claim:

1. A laser photocoagulator including a laser system and a viewing system, characterized in that the laser system includes a first solid state laser diode and at least one further solid state laser diode, said laser diodes operating in the infrared range, said laser system further including means for combining the infrared light produced by said laser diodes, and wherein said viewing system and said laser system have in common a dichroic beam splitter which, in use, separates infrared light from visible light, said viewing system and said laser system sharing a substantially common light path between said dichroic beam splitter and the eye of a patient, whereby the clinician may view a patient's eye through the beam splitter substantially without risk of exposure to the infrared light used for treatment, the photocoagulator further including an alignment system incorporating a visible light source, the visible light source comprising a solid state laser diode which provides coherent light having a wavelength in the visible range.

2. A photocoagulator as claimed in claim 1 wherein said infrared laser system diodes emit light with a wavelength of approximately 800 nm.

3. A photocoagulator as claimed in claim 1 wherein said dichroic beam splitter reflects infrared light and transmits visible light.

4. A photocoagulator as claimed in claim 1 wherein said laser system further includes means for reducing the magnification in one direction of the image which is produced on the retina of the eye of a patient by the infrared light.

5. A photocoagulator as claimed in claim 4 wherein said magnification reducing means comprises an anamorphic prism pair arranged so as to reduce the magnification of the image in its longest direction.

6. A photocoagulator as claimed in claim 1 wherein said laser system further includes optical means for providing an optimum beam diameter of the combined infrared light produced by said laser diodes which, in use, passes through the pupil of the patient's eye.

7. A photocoagulator as claimed in claim 6 wherein said optical means comprises a telescope.

8. A photocoagulator as claimed in claim 1, wherein said laser system additionally includes a beam combiner for causing the visible light from said alignment system to share the same optical path with the infrared laser light between said beam combiner and the eye of the patient.

9. A photocoagulator as claimed in claim 1 wherein said alignment system provides a plurality of beams of visible light incident on the retina, said beams being arranged to pass through different portions of the pupil such that if said photocoagulator is misaligned with the iris at least one of the beams will be at least partly blocked by the iris, and the pattern produced by the visible light on the retina also providing an indication of whether or not the infrared laser light is focused on the retina.

10. A photocoagulator as claimed in claim 9 wherein said beams of visible light converge to a spot or well defined pattern on the retina of the patient's eye when the infrared light is focused on the retina.

11. A photocoagulator as claimed in claim 9 wherein said beams of visible light are mutually non-parallel at the points of incidence on the patient's eye, whereby the configuration of a pattern produced on the retina of the patient's eye by the visible light is indicative of whether or not the infrared laser light is focused on the retina.

12. A photocoagulator as claimed in claim 11 wherein each of said beams of visible light has a non-circular cross-section when incident on the retina of the patient's eye, the relative alignment of the shapes produced on the retina being indicative of whether or not the infrared laser light is focused on the retina.

13. A photocoagulator as claimed in claim 11 wherein said non-parallel beams are provided by illuminating a target with a plurality of collimated beams of light.

14. A photocoagulator as claimed in claim 13 wherein said target is apertured and said non-parallel beams are generated by illuminating said target with said visible light to produce plural collimated beams and directing at least one of said collimated beams through a split field screen.

15. A photocoagulator as claimed in claim 14 wherein said non-parallel beams of visible light produce a cross-shaped pattern when the infrared light is focused on the retina and wherein said alignment system comprises a pair of split field screens disposed along the optical axis of the alignment system, the second of the screens being rotated by 90° with respect to the first.

16. A photocoagulator as claimed in claim 13 wherein said beams of visible light produce a cross-shaped pattern when the infrared laser light is focused on the retina.

17. A photocoagulator as claimed in claim 16 wherein said target comprises a circular disc formed with four slits disposed on orthogonal radii and extending inwardly towards, but without reaching, the center of said disc.

18. A photocoagulator as claimed in claim 17 wherein said alignment system further includes a pair of split field screens disposed along the optical axis of the alignment system, the second of the screens being rotated by 90° with respect to the first, said screens being incorporated in said target disc.

19. A photocoagulator as claimed in claim 1 wherein said viewing system may be aligned with a slit lamp and said photocoagulator further comprises a diverging lens positioned to be disposed between the slit lamp and the patient's eye whereby the focal point of the slit lamp will be moved further from the slit lamp.

20. A laser photocoagulator including a laser system and a viewing system, wherein the laser system includes a solid state laser diode which operates in the infrared range, and said viewing system and said laser system have in common a dichroic beam splitter which, in use, separates infrared light from visible light, said viewing system and said laser system sharing a substantially common light path between said dichroic beam splitter and the eye of a patient, whereby the clinician may view a patient's eye through the beam splitter substantially without risk of exposure to the infrared laser light used for treatment, the photocoagulator further comprising an alignment system, said alignment system including a visible light source and means for generating a plurality of non-parallel beams of visible light which are incident on the retina of the patient's eye, said means for generating said plural beams of visible light comprising an apertured target positioned to be illuminated by the visible light from said source and at least one split field screen, said beams of visible light being caused to pass through different portions of the pupil of the patient's eye such that if said photocoagulator is misaligned with the iris of the patient's eye at least one of the beams of visible light will be at least partly blocked by the iris, and the pattern of visible light produced on the retina by the incident visible light will provide an indication of whether or not the infrared laser light from the laser diode is focused on the retina.

21. A photocoagulator as claimed in claim 20, wherein said beams of visible light converge to a spot or well defined pattern on the retina when the infrared laser light is focused on the retina.

22. A photocoagulator as claimed in claim 20, wherein said non-parallel beams produce a cross-shaped pattern when the infrared laser light is focused on the retina.

23. A photocoagulator as claimed in claim 22, wherein said target comprises a circular disc formed with four slits disposed on orthogonal radii and extending inwards towards, but without reaching, the center of said disc.

24. A photocoagulator as claimed in claim 23 wherein said means for generating a plurality of non-parallel beams of visible light comprises a pair of split field screens disposed along the optical axis of the alignment system, the second of said screens being rotated by 90° with respect to the first of said screens, said screens being incorporated in the target disc.

25. A photocoagulator as claimed in claim 20, wherein said non-parallel beams of visible light produce a cross-shaped pattern when the infrared light is focused on the retina and said means for generating a plurality of non-parallel beams of visible light comprises a pair of split field screens disposed along the optical axis of the alignment system, the second of said screens being rotated by 90° with respect to the first of said screens.

26. A photocoagulator as claimed in claim 20 wherein said viewing system may be aligned with a slit lamp and said photocoagulator further comprises a diverging lens positioned to be disposed between the slit lamp and the patient's eye whereby the focal point of the slit lamp will be moved further from the slit lamp.

* * * * *